(12) United States Patent
Takagi et al.

(10) Patent No.: US 8,712,702 B2
(45) Date of Patent: Apr. 29, 2014

(54) MEASURING APPARATUS FOR MEASURING A PHYSICAL PROPERTY OF A SAMPLE

(75) Inventors: Takeshi Takagi, Kyoto (JP); Koji Okumura, Kyoto (JP); Tatsuo Kamata, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 273 days.

(21) Appl. No.: 13/167,585

(22) Filed: Jun. 23, 2011

(65) Prior Publication Data

US 2012/0158314 A1 Jun. 21, 2012

(30) Foreign Application Priority Data

Jun. 23, 2010 (JP) ................................. 2010-142244
Jun. 22, 2011 (JP) ................................. 2011-137934

(51) Int. Cl.
*G06F 19/00* (2011.01)
*G01N 1/10* (2006.01)

(52) U.S. Cl.
USPC .......................... 702/25; 435/287.1; 73/61.59

(58) Field of Classification Search
USPC .................... 702/25, 19; 73/61.59; 435/287.1
See application file for complete search history.

(56) References Cited

U.S. PATENT DOCUMENTS

| 5,168,046 | A | | 12/1992 | Hamamoto et al. | |
|---|---|---|---|---|---|
| 5,272,060 | A | | 12/1993 | Hamamoto et al. | |
| 5,998,184 | A | * | 12/1999 | Shi | ................................. 435/176 |
| 2007/0263195 | A1 | * | 11/2007 | Nagasaka et al. | ................ 355/53 |
| 2008/0118942 | A1 | * | 5/2008 | Sugiyama et al. | ............... 435/29 |
| 2008/0250849 | A1 | * | 10/2008 | Le Comte et al. | ........... 73/64.56 |
| 2009/0176030 | A1 | * | 7/2009 | Carlson et al. | ................ 427/487 |
| 2009/0323069 | A1 | * | 12/2009 | Naessens et al. | ............. 356/440 |
| 2010/0299072 | A1 | * | 11/2010 | Kamata et al. | .................. 702/19 |
| 2011/0300565 | A1 | * | 12/2011 | Furusato et al. | ................ 435/14 |
| 2012/0094367 | A1 | * | 4/2012 | Sugiyama et al. | ......... 435/287.1 |

FOREIGN PATENT DOCUMENTS

| JP | 07-037991 | | 2/1995 |
|---|---|---|---|
| JP | 7-37991 | * | 4/1995 |
| JP | H07-37991 B2 | | 4/1995 |
| JP | 09-033533 | | 2/1997 |
| JP | 9-33533 | * | 2/1997 |
| JP | H09-33533 A | | 2/1997 |
| JP | 09-318634 | | 12/1997 |
| JP | 9-318634 | * | 12/1997 |
| JP | H09-318634 A | | 12/1997 |
| JP | 2008-035748 A | | 2/2008 |
| WO | 2008-035748 A1 | | 3/2008 |

* cited by examiner

*Primary Examiner* — John Breene
*Assistant Examiner* — Ruihua Zhang
(74) *Attorney, Agent, or Firm* — Studebaker & Brackett PC

(57) ABSTRACT

A measuring apparatus for measuring a predetermined physical property of a liquid measuring sample comprises a preparing unit in which a plurality of materials including at least a liquid material are mixed; a supply route which supplies the liquid material to the preparing unit; a withdrawing unit which withdraws the measuring sample from the preparing unit into the supply route, the measuring sample being prepared to contain the liquid material supplied to the preparing unit via the supply route; and a measuring unit which measures the predetermined physical property of the measuring sample withdrawn into the supply route by the withdrawing unit.

21 Claims, 4 Drawing Sheets

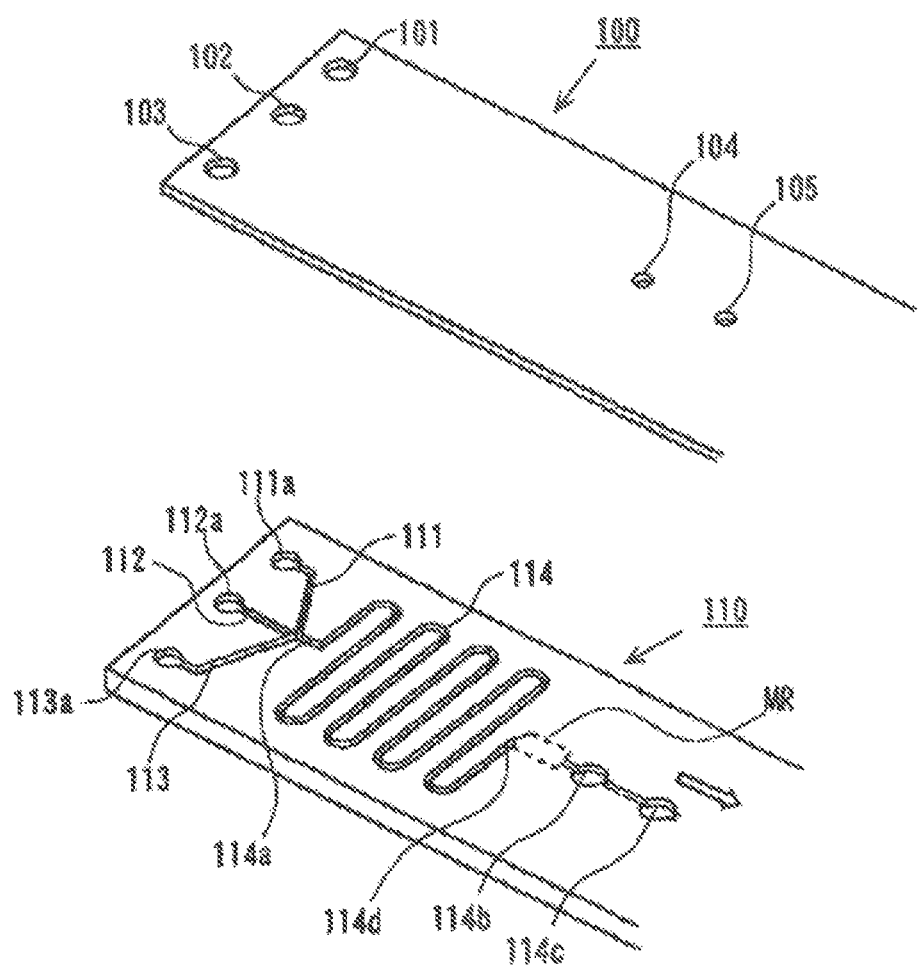

MEASURING APPARATUS FOR MEASURING A PHYSICAL PROPERTY OF A SAMPLE

CROSS-REFERENCE TO RELATED APPLICATION

This application claims the benefits of priority of the prior Japanese Patent Application No. 2010-142244 filed on Jun. 23, 2010 and the Japanese Patent Application No. 2011-137934 filed on Jun. 22, 2011, the entire contents of which are incorporated herein by reference.

FIELD OF THE INVENTION

The present invention relates to a measuring apparatus, a measuring method, a computer recording medium storing a measuring program, and a measuring system for measuring a physical property of a liquid measuring sample.

BACKGROUND OF THE INVENTION

As for a liquid measuring sample, when it is intended to measure a predetermined physical property of the concerning measuring sample for various purposes including, for example, physical, chemical, industrial, and agricultural purposes, a measuring apparatus is generally allowed to act on the concerning measuring sample by means of various techniques including, for example, electrical, optical, and chemical techniques. For example, when the plasma glucose concentration in blood of an examinee is measured in order to diagnose the diabetes, the measurement is generally performed on the basis of the current transition or change between electrodes by utilizing an enzyme including, for example, glucose oxidase (GOD) and glucose dehydrogenase (GDH) with respect to a measuring sample prepared from the blood (see, for example, Patent documents 1 to 3). On the other hand, in order to diagnose the diabetes, the glycohemoglobin concentration is measured for a measuring sample containing blood in some cases (see, for example, Patent documents 1 to 4).
[Patent document 1] Japanese Patent Publication No. 7-37991
[Patent document 2] Japanese Patent Application Laid-open No. 9-33533
[Patent document 3] Japanese Patent Application Laid-open No. 9-318634
[Patent document 4] International Publication No. 2008/035748

For example, when the measurement is performed for the predetermined purpose of, for example, the diagnosis of the diabetes with respect to an analysis objective originating from a living body including, for example, blood and urine, then a liquid measuring sample is prepared so that the concerning analysis objective is contained to successfully perform the appropriate measurement, and the measurement is performed for the measuring sample as described above. When the analysis is performed for various purposes including, for example physical, chemical, industrial, and agricultural purposes without being limited to the analysis in relation to the living body, then a liquid measuring sample containing the analysis objective is prepared, and the measurement is performed in a state of the liquid in many cases.

When it is intended to measure the physical property of the liquid measuring sample as described above, it is feared that any bubble contained in the liquid may inhibit the correct measurement. That is, in the case of the liquid measuring sample, there is such a possibility that the bubble may enter the liquid measuring sample, for example, during the preparation process and/or the supply process for supplying the liquid. It is difficult to correctly measure the physical property due to the presence of the bubble depending on the technique of the measurement.

SUMMARY OF THE INVENTION

The present invention has been made taking the foregoing problem into consideration, an object of which is to provide a measuring apparatus, a measuring method, a measuring program, and a measuring system constructed to more correctly execute the measurement of a physical property of a liquid measuring sample.

In order to solve the problem as described above, the present invention adopts such an arrangement that a measuring unit, which performs the measurement for a liquid measuring sample, is installed on the upstream side of a preparing unit for preparing the measuring sample, i.e., on a supply route for supplying at least one liquid material of materials of the measuring sample to the preparing unit. According to this arrangement, any liquid always exists in an area in which the measurement is performed by the measuring unit. Therefore, the measuring area, in which the measurement is performed, can be maintained in such a state that any bubble does not exist as far as possible. Thus, it can be expected to perform the correct measurement.

In particular, the present invention resides in a measuring apparatus for measuring a predetermined physical property of a liquid measuring sample; the measuring apparatus comprising a preparing unit which prepares the measuring sample; a supply route which supplies a liquid material to the preparing unit in order to prepare the measuring sample; a withdrawing unit which withdraws the measuring sample from the preparing unit into the supply route, the measuring sample being prepared by supplying the liquid material to the preparing unit via the supply route; and a measuring unit which measures the predetermined physical property of the measuring sample withdrawn into the supply route by the withdrawing unit.

The measuring apparatus according to the present invention is the apparatus for measuring the predetermined physical property of the measuring sample. The measuring sample, which is the measurement objective thereof, is the liquid during the measurement. The measuring sample is prepared in the preparing unit by supplying the liquid material to the preparing unit. The measuring sample may be constructed by the liquid material singly. Alternatively, the measuring sample may be obtained by mixing a plurality of liquid materials. When the liquid material is supplied to the preparing unit via the supply route, the liquid material is in a liquid state. Therefore, when the liquid material is supplied, the supply route is filled with the liquid material.

In order to measure the predetermined physical property of the measuring sample by the measuring unit after preparing the measuring sample in the preparing unit, the liquid measuring sample, which exists in the preparing unit, is withdrawn (pulled in) into the supply route by the withdrawing unit. That is, the withdrawing unit withdraws the liquid measuring sample into the supply route which is filled with the liquid material. As a result, the liquid material is progressively replaced (substituted) with the measuring sample, as starting from the area disposed near to the preparing unit in the supply route, while mixing the existing liquid material and the measuring sample with each other depending on circumstances.

When the substitution is performed from the liquid material to the measuring sample in the supply route as described above, the interior of the supply route is in the state of being always filled with any liquid. That is, although the situation of replacement from the liquid material to the measuring sample is changed depending on the cross-sectional area of the supply route and the viscosities of the liquid material and the measuring sample, at least the interior of the supply route is filled with the liquid material, the measuring sample, or the mixture liquid of the both liquids. Therefore, it is possible to suppress the appearance of any bubble in the supply route as far as possible during the period in which the withdrawing operation is performed by the withdrawing unit. As a result, even when the measuring unit measures the measuring sample withdrawn by the withdrawing unit in the supply route, then it is scarcely feared that any influence may be exerted by the bubble, and it is possible to expect that the predetermined physical property is measured more correctly.

Any measuring means may be used in relation to the measuring unit provided for the measuring apparatus according to the present invention provided that the measuring means can measure the predetermined physical property of the measuring sample. For example, the measuring unit may perform the measurement by means of optical means for measuring the predetermined physical property of the measuring sample on the basis of the data which relates to the received light and which is obtained such that the measuring light is radiated onto the measuring sample and the light, which is emitted from the measuring sample to the outside, is received. The measurement, which is performed by the measuring unit as described above, is exemplified, for example, by the measurement of the absorbance performed by optical means, the measurement of the color of the sample based on the transmitted light obtained by transmitting the measuring light through the measuring sample, and the measurement of the concentration of a predetermined component by utilizing the transmitted light as exemplified by the liquid chromatography. The measuring sample may be any liquid measurement objective. The object or purpose of the measurement is not limited to the purpose concerning the living body, which may be various purposes including, for example, physical, chemical, industrial, and agricultural purposes.

In this context, when the measuring sample is withdrawn by the withdrawing unit as described above, a mixture liquid of the existing liquid material and the measuring sample is provided or produced in the supply route in some cases. The appearance of the mixture liquid can be sometimes neglected depending on the viscosities of the both liquids and the cross-sectional area of the supply route. However, in some cases, when the measuring sample is withdrawn by the withdrawing unit, a relatively large amount of the mixture liquid may be possibly produced. In such a situation, if the mixture liquid exists in the predetermined area in which the liquid as the objective of the measurement performed by the measuring unit is to be positioned, the correct measurement of the predetermined physical property of the measuring sample may be disturbed. In view of the above, taking this problem into consideration, the measuring apparatus may be constructed such that the withdrawing unit withdraws the measuring sample from the preparing unit so that a mixture liquid of the measuring sample and the liquid material contained in the supply route, which is produced when the measuring sample is withdrawn into the supply route, is moved beyond a predetermined measuring area disposed in the supply route in order to perform the measurement by the measuring unit.

When the measuring apparatus is constructed as described above, even if the mixture liquid is produced when the measuring sample is withdrawn by the withdrawing unit, then the mixture liquid is withdrawn to arrive at the position at which the mixture liquid is moved beyond the predetermined measuring area in the direction in which the mixture liquid flows upstream from the measuring unit along the supply route, i.e., in the direction of withdrawal of the measuring sample. Therefore, the objective of the measurement performed by the measuring unit can be reliably the measuring sample. As for the substitution of the mixture liquid with the measuring sample, it is possible to judge that the substitution is completed if it is possible to judge that the ratio occupied by the measuring sample is increased to such an extent that any influence is not exerted on the measurement performed by the measuring unit.

In this context, the measuring apparatus as described above may further comprise a supply route discharge section which discharges the measuring sample existing in the supply route to the preparing unit after the predetermined physical property of the measuring sample is measured by the measuring unit; and a preparing unit discharge section which discharges any liquid contained in the preparing unit to outside of the preparing unit. The liquid may be discharged by the preparing unit discharge section in synchronization with the discharge performed by the supply route discharge section. The measuring apparatus may be constructed such that the interior of the supply route is maintained in a state of being filled with the liquid material when the liquid contained in the preparing unit is discharged by the preparing unit discharge section.

According to this arrangement, when the measurement by the measuring unit is completed, then the measuring sample contained in the supply route is discharged, and the liquid contained in the preparing unit is discharged. Thus, it is possible to provide for the preparation of the next measuring sample and the measurement of the predetermined physical property thereof. In this situation, the interior of the supply route is in the state of being filled with the liquid material. Therefore, the area, in which the measurement is to be performed by the measuring unit, is filled with the liquid. Thus, the possibility for the bubble to enter the area is excluded as far as possible.

When the arrangement as described above is adopted, it is also preferable that the supply route and the preparing unit are communicated with each other via a communication hole which has such a predetermined cross-sectional area that any air contained in the preparing unit does not enter the supply route when the discharge by the supply route discharge section is completed, the liquid contained in the preparing unit is discharged by the preparing unit discharge section, and a liquid level in the preparing unit is lower than a position of communication between the supply route and the preparing unit. When the communication hole, which makes communication between the supply route and the preparing unit, has the relatively small cross-sectional area, the movement of the liquid hardly occurs from the supply route to the preparing unit, unless any pressure is applied to the interior of the supply route. Accordingly, it is possible to suppress the invasion of the air from the preparing unit into the supply route when the liquid is discharged by the preparing unit discharge section, by determining the cross-sectional area of the communication hole while considering, for example, the viscosity of the liquid material and the cross-sectional area of the supply route. The specified form of communication between the supply route and the preparing unit is not limited to the form in which the communication hole is used as described above.

In this context, the measuring apparatus as described above may be constructed such that the measuring sample is prepared by mixing, in the preparing unit, blood, a hemolytic agent which hemolyzes the blood, and a diluent which is supplied as the liquid material via the supply route to the preparing unit and which dilutes the blood. Accordingly, the predetermined physical property of the measuring sample containing the blood hemolyzed by the hemolytic agent is measured by the measuring apparatus according to the present invention.

Further, the measuring apparatus as described above may be such an apparatus that a plasma glucose concentration of the blood is calculated on the basis of the predetermined physical property of the measuring sample prepared to contain the blood. In this arrangement, the measuring unit measures a hemoglobin concentration in the measuring sample withdrawn into the supply route by the withdrawing unit, as the predetermined physical property by means of optical means.

The measuring apparatus as described above may further comprise a sample glucose concentration measuring unit which measures a glucose concentration of the measuring sample prepared in the preparing unit; and a plasma glucose concentration calculating unit which calculates a plasma glucose concentration of the blood on the basis of the glucose concentration measured by the sample glucose concentration measuring unit and the hemoglobin concentration measured by the measuring unit. According to this arrangement, the plasma glucose concentration calculating unit calculates the plasma glucose concentration of the blood of the living body as the analysis objective on the basis of the measurement result obtained by the sample glucose concentration measuring unit and the measurement result obtained by the measuring unit. That is, in the case of the concerning apparatus, the measuring sample, which is in the hemolyzed state, is prepared by mixing the hemolytic agent, the diluent, and the blood without extracting any plasma component from the blood, for example, by means of the centrifugation. Further, the hemoglobin concentration, which is the predetermined physical property of the measuring sample, is correctly measured by the measuring unit, and the obtained result is taken into consideration in combination with the measurement result obtained by the sample glucose concentration measuring unit. Accordingly, it is possible to correctly calculate the plasma glucose concentration of the blood. The hemoglobin concentration described above refers to the concentration in the sample of hemoglobins of all types, without being limited to the type of hemoglobin.

In this context, in the measuring apparatus as described above, the sample glucose concentration measuring unit may measure the glucose concentration of the measuring sample contained in the preparing unit in a state of being exposed to the measuring sample in the preparing unit. When the measurement of the glucose concentration is directly carried out with respect to the measuring sample contained in the preparing unit, it is possible to shorten the time required for the measurement. Alternatively, the sample glucose concentration measuring unit may measure the glucose concentration of the measuring sample in the supply route in a state of being exposed to the measuring sample withdrawn into the supply route by the withdrawing unit. That is, in this form, the withdrawal of the measuring sample, which is performed by the withdrawing unit, is also utilized for the measurement of the glucose concentration.

In this arrangement, it is preferable that the sample glucose concentration measuring unit is installed in the supply route between the measuring unit and the preparing unit. As described above, the mixture liquid of the liquid material and the measuring sample is formed when the measuring sample is withdrawn by the withdrawing unit. Based on this fact, when the sample glucose concentration measuring unit is installed in the supply route between the measuring unit and the preparing unit, it is possible to measure the glucose concentration of the measuring sample more reliably.

The range, in which the present invention is applicable, is not limited by the size and the shape of any specified measuring apparatus. For example, the technical concept of the present invention is applicable not only to the measuring apparatus generally having the macro size which is based on the use of, for example, the dilution tank or vessel and the nozzle but also to the measuring apparatus which has the micro structure including, for example, the microdevice.

In another aspect, the present invention can be also recognized from a viewpoint of the measuring method. That is, the present invention resides in a measuring method for measuring a predetermined physical property of a liquid measuring sample prepared in a preparing unit by supplying a liquid material to the preparing unit via a supply route; the measuring method comprising a withdrawing step of withdrawing the measuring sample from the preparing unit into the supply route, the measuring sample being prepared by supplying the liquid material to the preparing unit via the supply route; and a measuring step of measuring the predetermined physical property of the measuring sample withdrawn into the supply route in the withdrawing step. Also in the measuring method according to the present invention, it is possible to suppress the invasion of the bubble into the measuring sample during the measurement in the measuring step, and thus it is possible to correctly measure the predetermined physical property of the measuring sample in the same manner as in the measuring apparatus described above.

For example, the predetermined physical property of the measuring sample may be measured by optical means in the measuring step. The measuring method may further comprise a supply route discharging step of discharging the measuring sample existing in the supply route to the preparing unit after measuring the predetermined physical property of the measuring sample in the optical measuring step; and a preparing unit discharging step of discharging any liquid contained in the preparing unit to outside of the preparing unit after the discharge performed in the supply route discharging step or in synchronization therewith. In this procedure, when the liquid contained in the preparing unit is discharged in the preparing unit discharging step, the interior of the supply route is maintained in a state of being filled with the liquid material. According to the measuring method as described above, the area, in which the measurement is to be performed in the optical measuring step, can be filled with the liquid even when the measurement of the predetermined physical property is prepared for the next measuring sample. Thus, it is possible to avoid such a situation that any influence is exerted by the bubble when the next measurement is performed.

In still another aspect, the present invention can be also recognized from a viewpoint of a non-transitory computer recording medium storing a measuring program. That is, the present invention resides in a non-transitory computer recoding medium storing a measuring program for measuring a predetermined physical property of a liquid measuring sample prepared in a preparing unit by supplying a liquid material to the preparing unit via a supply route by means of a computer; wherein the measuring program allows the computer to execute a withdrawing step of withdrawing the measuring sample from the preparing unit into the supply route, the measuring sample being prepared by supplying the liquid material to the preparing unit via the supply route; and a measuring step of measuring the predetermined physical property of the measuring sample withdrawn into the supply route in the withdrawing step. Also in the recording medium storing the measuring program according to the present invention, it is possible to suppress the invasion of the bubble into the measuring sample during the measurement in the measuring step, and thus it is possible to correctly measure the predetermined physical property of the measuring sample in the same manner as in the measuring apparatus described above.

In still another aspect, the present invention can be also recognized from a viewpoint of the measuring system. That is, the present invention resides in a measuring system for measuring a predetermined physical property of a liquid measuring sample; the measuring system comprising a preparing device which prepares the measuring sample; a supply route which supplies a liquid material to the preparing device in order to prepare the measuring sample; a withdrawing device which withdraws the measuring sample from the preparing device into the supply route, the measuring sample being prepared by supplying the liquid material to the preparing device via the supply route; and a measuring device which measures the predetermined physical property of the measuring sample withdrawn into the supply route by the withdrawing device. The technical concept, which has been disclosed in relation to the measuring apparatus described above, is also applicable to the measuring method, the recording medium storing the measuring program, and the measuring system according to the present invention in the same manner as described above.

According to the present invention, the measuring area, in which the measurement is to be performed, can be maintained in the state in which the bubble does not exist as far as possible. According to the present invention, it is possible to provide the measuring apparatus, the measuring method, the measuring program, and the measuring system constructed to more correctly execute the measurement of the physical property of the liquid measuring sample.

BRIEF DESCRIPTION OF THE DRAWINGS

FIG. 4 shows a second specified arrangement of a measuring apparatus according to the present invention.

DETAILED DESCRIPTIONS OF THE EMBODIMENTS

An explanation will be made below with reference to the drawings about a measuring apparatus according to an embodiment to carry out the present invention. The following embodiment is constructed by way of example, and the present invention is not limited to the construction or arrangement of the embodiment.

[First Embodiment]
<Outline of Measuring Apparatus>

Figure 1:
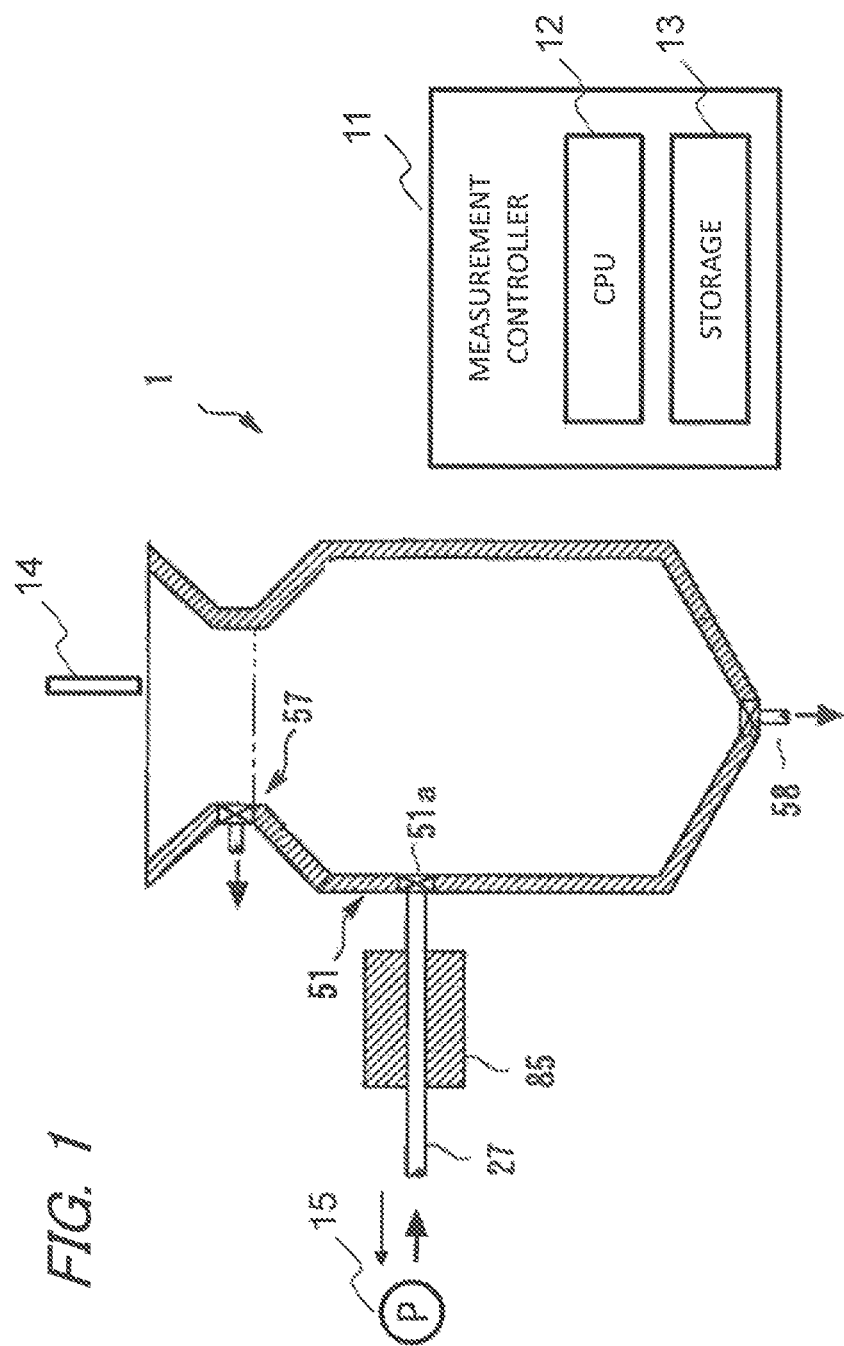
FIG. 1 shows an arrangement of a part of a measuring apparatus according to the present invention.

FIG. 1 shows a partial arrangement of a measuring apparatus 1 according to the present invention. The measuring apparatus of this embodiment comprises a preparing unit (dilution vessel) 51 in which a measuring sample is prepared, a supply route (supply passage) 27 which supplies a liquid material to the preparing unit in order to prepare the measuring sample, a withdrawing unit (not shown) which withdraws the measuring sample from the preparing unit 51 into the supply route 27, the measuring sample being prepared by supplying the liquid material to the preparing unit 51 via the supply route 27, and a measuring unit 85 which measures a predetermined physical property of the measuring sample withdrawn into the supply route 27 by the withdrawing unit. The measuring apparatus according to the present invention can measure the plasma glucose concentration and the glycohemoglobin concentration in order to diagnose the diabetes. The measuring apparatus comprises therein all constitutive parts or components required for the purpose, including the measuring unit 85, a glucose measuring mechanism, a glycohemoglobin measuring mechanism, and a measurement control unit for processing the measured values supplied from the mechanisms (any one of them is not shown). In this embodiment, the measuring unit 85 is an absorbance meter.

The measuring sample is prepared in the dilution vessel 51, for example, such that a diluent (dilution liquid) and a hemolytic liquid (hemolytic agent) are mixed with a specimen (blood) as the analysis objective. The diluent and the hemolytic liquid are supplied to the dilution vessel 51 via the supply route 27 as described above. In this arrangement, in the embodiment of the present invention, the measuring sample, which is prepared in the dilution vessel 51, is subjected to respective analytical processes in the glucose measuring mechanism (not shown). The glucose measuring mechanism has a sensor unit (sensor), a power source unit (power source), and a current value measuring unit (current meter) (any one of them is not shown). Although not shown, the glucose measuring mechanism itself is provided in the dilution vessel 51. The sensor unit outputs the electrical physical quantity (current value) corresponding to the quantity or amount of electrons given and received with respect to glucose contained in the measuring sample. The sensor unit has an enzyme-immobilized layer in which glucose oxidoreductase is immobilized, and an electrode which gives and receives electrons with respect to the enzyme reaction product produced in the enzyme-immobilized layer. In this embodiment, the sensor unit is installed on the wall surface of the dilution vessel 51 so that the enzyme-immobilized layer and the electrode are exposed to the measuring sample contained in the dilution vessel 51. The sensor unit can repeatedly measure glucose. Those adoptable as the oxidoreductase contained in the enzyme-immobilized layer include glucose oxidase (GOD) and glucose dehydrogenase (GDH). When GOD is adopted as the enzyme, a hydrogen peroxide electrode is adopted as the electrode corresponding to GOD. This embodiment will be explained below assuming that GOD is adopted as the enzyme. However, it is not intended that the enzyme, which can be adopted, is limited to GOD.

When the voltage is applied by the power source unit in the state in which the sensor unit is exposed to the measuring sample, the current is allowed to flow between the electrodes included in the sensor unit. The current value measuring unit measures the current between the electrodes, and the measured value is fed to the measurement control unit (measurement controller) 11. In relation to the measurement of glucose, the measurement result of the absorbance, which is obtained at the absorption wavelength of hemoglobin by the absorbance meter 85, is also fed to the measurement control unit.

The absorbance meter 85 is arranged on the supply route 27 in the vicinity of the connecting portion between the supply route 27 and the dilution vessel 51. The absorbance meter 85 can measure the absorbance of the liquid allowed to flow through the supply route 27 in the vicinal area.

The absorbance meter 85 radiates the light having the absorption wavelength of hemoglobin onto the supply route 27 to measure the absorbance. The absorbance meter 85 has a light-emitting laser diode and a light-receiving photodiode. The light-emitting laser diode radiates the light onto the measuring sample allowed to flow through the supply route 27, and the light, which is transmitted through the measuring sample, is received by the light-receiving photodiode.

Figure 2:
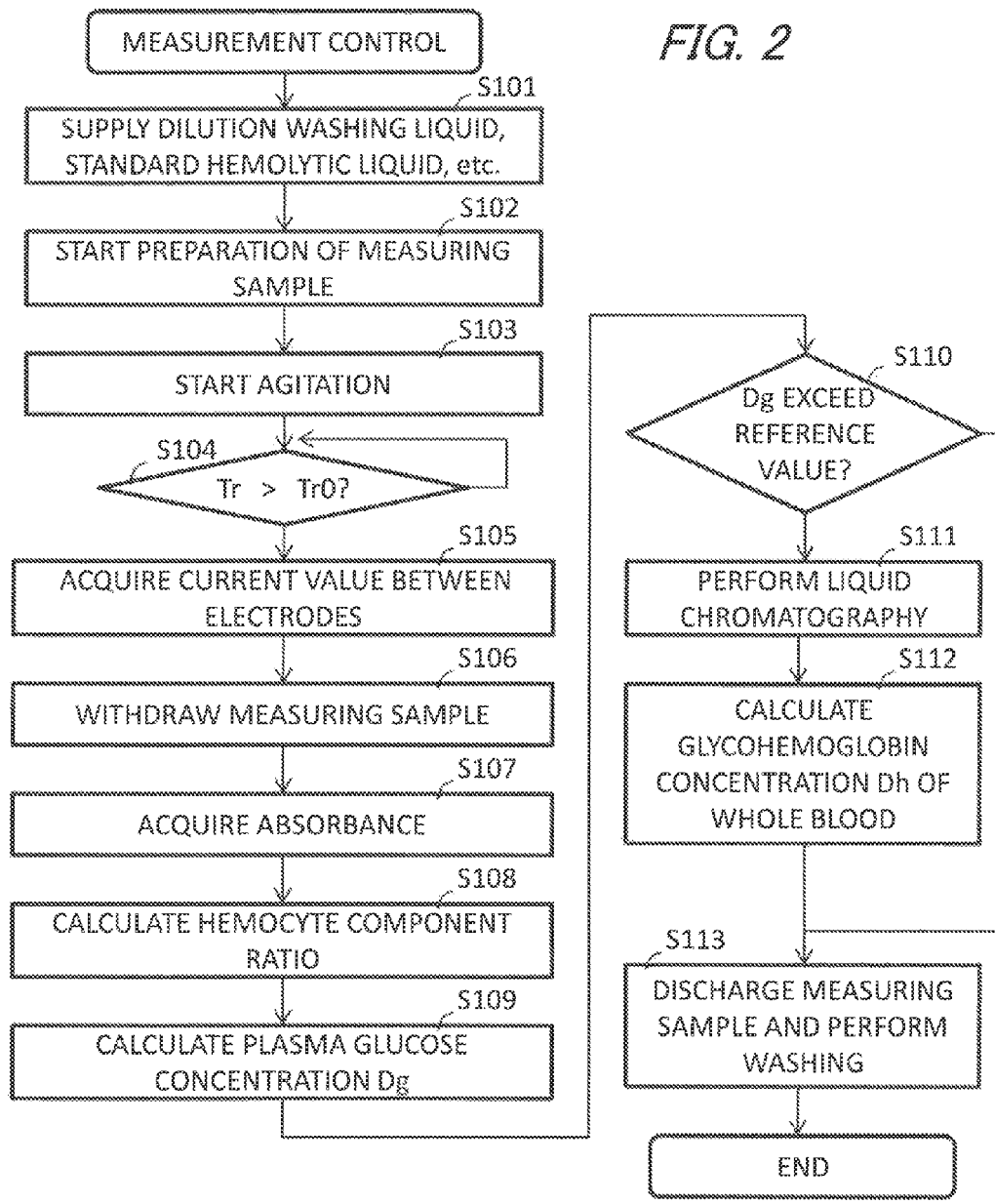
FIG. 2 shows a flow chart illustrating the measurement control for a measuring sample to be executed in the measuring apparatus shown in FIG. 1.

An explanation will now be made on the basis of FIG. 2 about the measurement control of the glucose measuring mechanism and the glycohemoglobin measuring mechanism in relation to the measuring apparatus of this embodiment. The measurement control shown in FIG. 2 is realized by executing a program recorded in a memory included in the measurement controller 11 which is provided as the computer as well. The measurement controller 11 includes, at least, a central processing unit (CPU) 12 which is one of microprocessors, a storage (recording media) 13, and input/output units (I/O). For example, the storage 13 includes memories, such as a read only memory (ROM) and a random access memory (RAM), for storing programs and data. The RAM is used as a work area for the CPU. The storage 13 may further include auxiliary storage unit(s), such as a hard disc for storing several data and/or programs. The CPU 12 loads the program stored in the ROM to the RAM and executes the program. By the execution of the program, the measurement controller, for the measurement control exemplified in FIG. 2, controls operations of opening valves 57 and 58, a nozzle 14, the glucose measuring mechanism (sensor, power source, current meter), a pump 15, and the absorbance meter 85. The measurement control shown in FIG. 2 resides in the measuring process for the index in order to diagnose the diabetes. Specifically, the measurement control is executed by operating an operation panel provided distinctly for the measuring apparatus 1 by a user so that the instruction is given to start the measurement.

At first, in S101, the materials including, for example, the diluent and the hemolytic liquid are supplied to the dilution vessel 51 in order to prepare the measuring sample. The materials can be supplied directly into the dilution vessel 51 via the supply route 27. The dilution vessel 51 has an opening valve 57 and an opening valve 58. When the materials (liquids) are supplied to perform the preparation, then the opening valve 57 is in the valve-open state, and the opening valve 58 is in the valve-closed state. When the opening valve 57 is in the valve-open state as described above, the mixture liquid of the standard hemolytic liquid and the diluent in a constant amount is supplied into the dilution vessel 51. When the process of S101 is completed, the procedure proceeds to S102.

In S102, the blood (whole blood), which is the analysis objective, is added to the dilution vessel 51 to which the materials have been supplied as described above, and the measuring sample is prepared thereby. Specifically, a nozzle 14, which accommodates the blood, discharges the blood contained in the nozzle into the dilution vessel 51 after the process of S101 described above. The blood is mixed with the mixture liquid having been produced, and thus the measuring sample is prepared. When the process of S102 is completed, the procedure proceeds to S103.

In S103, the stirring or agitation of the measuring sample is started. The agitation is performed by operation of an agitator (not shown) under control of the measurement controller 11. The agitation facilitates the hemolysis. When the process of S103 is completed, the procedure proceeds to S104.

In S104, it is judged whether or not the hemolysis time Tr exceeds the reference hemolysis time Tr0. If the affirmative judgment is given in S104, the procedure proceeds to S105. If the negative judgment is given, the process of S104 is repeated again.

In S105, the detected value obtained by the sensor unit of the glucose measuring mechanism, i.e., the current value allowed to flow through the hydrogen peroxide electrode is acquired. In this embodiment, the current value allowed to flow between the electrodes is measured by the current value measuring unit at the point in time at which the hemolysis time Tr arrives at the reference hemolysis time Tr0. The measured value is delivered to the measurement controller 11.

When the process of S105 described above is completed, the procedure proceeds to S106. In S106, a part of the measuring sample contained in the dilution vessel 51 is withdrawn (pulled in) into the supply route 27. The pump 15, which is communicated with the dilution vessel 51 via the supply route 27, is installed in the analyzer (analyzing apparatus). The part of the measuring sample is withdrawn into the supply route 27 in accordance with the action of the pump 15. The hemoglobin concentration can be measured on the basis of the absorbance of the measuring sample measured by the absorbance meter 85 provided for the supply route 27. The diluent, with which the supply route has been filled, is mixed with the measuring sample immediately after the execution of the withdrawal. Therefore, the withdrawal is performed to such an extent that the mixture liquid is separated sufficiently far from the measuring area of the absorbance meter 85. The withdrawal of the measuring sample into the supply route 27 by the aid of the pump 15 corresponds to the withdrawal performed by the withdrawing unit according to the present invention. When the process of S106 is completed, the procedure proceeds to S107.

In S107, the absorbance of the measuring sample is measured at the absorption wavelength of hemoglobin by means of the absorbance meter 85, and the measured value is delivered to the measurement controller 11. In the measurement control unit, the hemoglobin concentration of the measuring sample is calculated on the basis of the measured value. When the process of S107 is completed, the procedure proceeds to S108.

In the measurement control, the hemoglobin concentration of the measuring sample is measured by the absorbance meter 85 when the plasma glucose concentration is calculated. The absorbance meter 85 measures the absorbance of the measuring sample such that the measuring light for the measurement is radiated onto the measuring sample from the light-emitting laser diode, and the light, which is transmitted through the measuring sample, is received by the light-receiving photodiode. Therefore, if any bubble is contained in the measuring sample, then the measuring light is scattered thereby, and it is difficult to measure the correct absorbance.

However, in this embodiment, as shown in FIGS. 3A to 3D, the supply route 27 is always filled with any liquid. Therefore, the problem of the scattering of the measuring light, which is caused by the bubble as described above, is hardly caused.

Figure 3A:
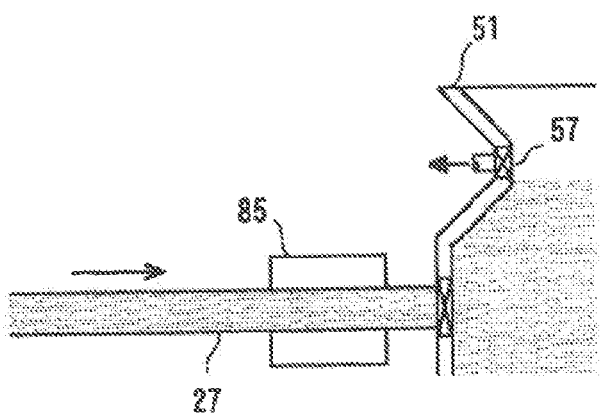
FIG. 3A shows a first drawing illustrating a situation of movement of the liquid in a dilution vessel and a supply route when the measurement control shown in FIG. 2 is performed.
Figure 3B:
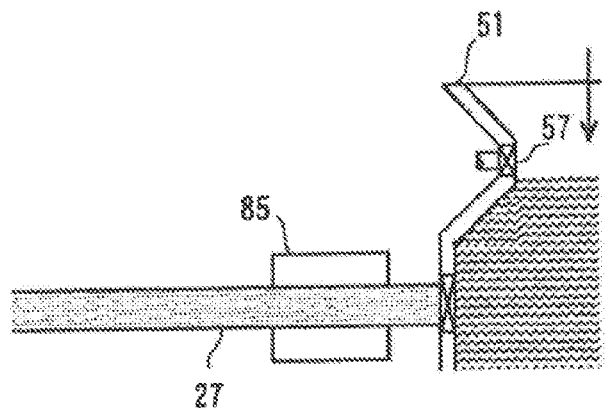
FIG. 3B shows a second drawing illustrating a situation of movement of the liquid in the dilution vessel and the supply route when the measurement control shown in FIG. 2 is performed.
Figure 3C:
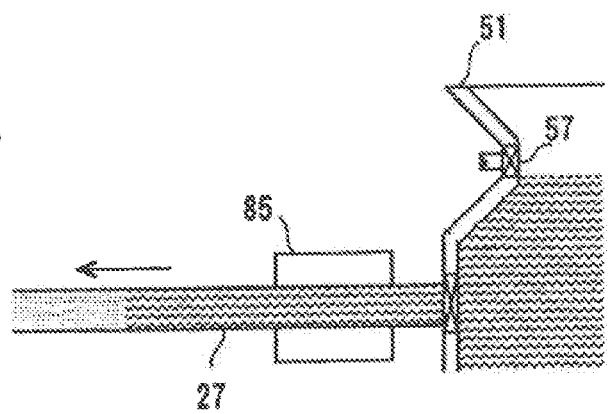
FIG. 3C shows a third drawing illustrating a situation of movement of the liquid in the dilution vessel and the supply route when the measurement control shown in FIG. 2 is performed.

This feature will be explained in detail. When the diluent is supplied to the dilution vessel 51 (during the process of S101 described above), as shown in FIG. 3A, the supply route 27 is filled with, for example, the diluent fed from, for example, a diluent bottle installed distinctly in the measuring apparatus. Subsequently, when the blood as the analysis objective is added to the dilution vessel 51 by the nozzle (during the processes of S101 and S102 described above), then the measuring sample is merely prepared in the dilution vessel 51 as shown in FIG. 3B, and the phenomenon, in which any bubble appears in the supply route 27, is not caused.

Figure 3D:
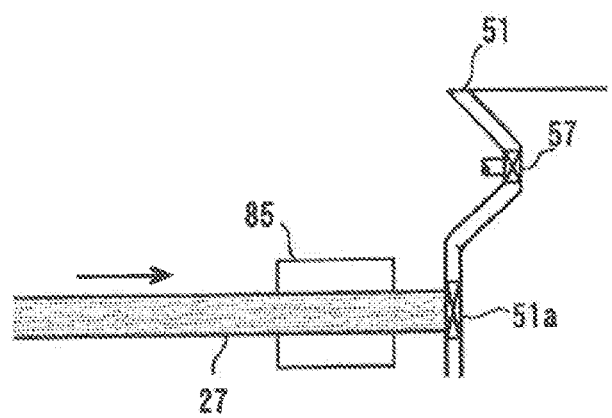
FIG. 3D shows a fourth drawing illustrating a situation of movement of the liquid in the dilution vessel and the supply route when the measurement control shown in FIG. 2 is performed.

Further, when the measuring sample is withdrawn into the supply route 27 in order to measure the absorbance (during the process of S105 described above), as shown in FIG. 3C, the diluent does not exit but the measuring sample exists in the measuring area disposed inside the absorbance meter 85. In this situation, any bubble does not appear in the supply route 27 as well. As described above, the sufficient amount of the measuring sample is withdrawn into the supply route 27 during the withdrawal so that the mixture liquid of the diluent and the measuring sample does not exert any influence on the absorbance meter 85. When the analysis process for the blood is completed, and the measurement control comes to the end (upon the completion of the process of S113 described above), then the interior of the supply route 27 is filled with the diluent again as shown in FIG. 3D. Also in this situation, the phenomenon, in which any bubble appears in the supply route 27, is not caused.

When the analysis process for the blood is completed, and the measurement control comes to the end (upon the completion of the process of S113 described above), then the measuring sample, which exists in the supply route 27, is fed to the dilution vessel 51 by means of the pump, and the liquid contained in the dilution vessel 51 is discharged by allowing the opening valve 58 to be in the valve-open state in the dilution vessel 51. In this arrangement, the supply route 27 and the dilution vessel 51 are communicated with each other at the communication position 51a via the communication hole having the cross-sectional area which is extremely smaller than the cross-sectional area of the supply route 27. As shown in FIG. 3D, the communication hole has the small cross-sectional area to such an extent that the air does not invade into the supply route 27 when the liquid contained in the dilution vessel 51 is discharged, the liquid level thereof is lower than the communication position 51a, and the air is stored in the dilution vessel 51. Therefore, an appropriate value is adopted for the cross-sectional area of the communication hole on the basis of, for example, the physical property of the diluent, especially the viscosity thereof and the cross-sectional area of the supply route 27. When the process of S113 is completed, then the interior of the supply route 27 is filled with the diluent again as shown in FIG. 3D, and any bubble does not make invasion thereinto from the side of the dilution vessel 51.

As described above, the bubble is reliably suppressed in the supply route 27 for which the absorbance meter 85 is arranged when the measurement control is performed. Therefore, it is possible to reliably perform the measurement of the absorbance by the absorbance meter 85. This remarkable effect is provided owing to the fact that the absorbance meter 85 is arranged on the upstream side of the dilution vessel 51 in the direction in which the diluent is supplied in the supply route 27 as shown in FIGS. 1 and 3. That is, the supply route 27, which supplies the diluent to the dilution vessel 51, is always filled with the diluent during the supply. Taking notice of this fact, the measuring sample, which is produced in the dilution vessel 51 positioned on the downstream side from the absorbance meter 85, is intentionally withdrawn to the upstream side to measure the absorbance. When the arrangement as described above is adopted, it is possible to avoid the occurrence of such a state that no liquid exists in the measuring area of the absorbance meter. Therefore, the absorbance meter 85 can perform the appropriate or proper measurement.

<First Modified Embodiment>

In the embodiment described above, the sensor unit of the glucose measuring mechanism is provided in the dilution vessel 51 in combination. In place of this arrangement, the sensor unit may be installed on the supply route 27 in the vicinity of the absorbance meter 85. As described above, the measuring sample is withdrawn into the supply route 27 in the vicinity of the absorbance meter 85. Therefore, even when the sensor unit is arranged on the supply route in the vicinity of the absorbance meter 85, it is possible to measure the correct plasma glucose concentration of blood in the same manner as in the embodiment described above. In this arrangement, it is preferable that the sensor unit is installed on the supply route 27 between the absorbance meter 85 and the dilution vessel 51.

<Second Modified Embodiment>

The measurement of the plasma glucose concentration, which is based on the use of the absorbance of the measuring sample as described above, is not limited to the macro size blood analyzer which uses, for example, the dilution vessel and the nozzle. The measurement of the plasma glucose concentration is also applicable to all types of blood analyzers including, for example, a blood analyzer which uses a microdevice. In the case of the microdevice, the flow passage, through which the sample or the like is allowed to flow, has the widthwise dimension and the depth dimension which are formed in the order of micrometer. Accordingly, the liquid such as the sample or the like can be moved by utilizing the capillary phenomenon. When the microdevice is utilized, it is possible to miniaturize the blood analyzer.

A microdevice shown in FIG. 4 realizes the measurement which is the same as or equivalent to the measurement of the plasma glucose concentration described in the foregoing embodiment. Specifically, a measuring sample, which is prepared by mixing blood as the analysis objective, a diluent, and a standard hemolytic liquid, is subjected to the measurement of the sample glucose concentration performed by an electrode based on the use of a GOD film (corresponding to the measurement performed by the sensor unit as described above) and the measurement performed by an optical system in order to measure the absorbance (corresponding to the measurement performed by the absorbance meter 85 as described above). Accordingly, the measurement of the plasma glucose concentration is finally realized. FIG. 4 mainly shows the construction of flow passages of the microdevice provided for the preparation of the measuring sample and the measurement of the plasma glucose concentration. As for a measuring device (measuring apparatus) for measuring the physical property of the measuring sample, a measuring area (measuring region) MR, in which the measuring device is installed, is shown by dotted lines in FIG. 4.

The microdevice shown in FIG. 4 is formed such that a cover 100 is stacked on a substrate 110 formed with the flow passages, with an unillustrated joining sheet intervening therebetween. In this arrangement, the cover 100 is formed, for example, such that the punching processing is applied to a transparent resin film, and then the resin film is cut to have an aimed size. In the punching processing, a plurality of through-holes are formed to provide a first introducing port 101 into which the diluent is introduced, a second introducing port 102 into which the standard hemolytic liquid is introduced, a blood introducing port 103 into which the blood is introduced, and air vent holes 104, 105. It is of course allowable that the punching processing is applied after cutting the resin film to form the cover 100 as well. It is preferable that a hydrophilic or water-attracting treatment is applied to one surface of the cover 100, for example, by applying a surfactant or radiating the ultraviolet ray.

The flow passages, which have recess-shaped cross sections, are formed on the substrate 110. The flow passages, which are formed on the substrate 110, include a first supply flow passage 111, a second supply flow passage 112, a blood supply flow passage 113, and a diluting flow passage 114. The diluent is introduced from the first introducing port 101, the standard hemolytic liquid is introduced from the second introducing port 102, and the blood is introduced from the blood introducing port 103. These liquids are allowed to flow through the first supply flow passage 111, the second supply flow passage 112, and the blood supply flow passage 113 respectively in accordance with the capillary phenomenon. The first supply flow passage 111, the second supply flow passage 112, and the blood supply flow passage 113 are connected to an end portion 114a of the diluting flow passage 114 respectively. The diluting flow passage 114 is formed to have a meander shape which meanders in a bellows form. Accordingly, the mixing of the blood, the diluent, and the standard hemolytic liquid is accelerated. In this arrangement, a recessed portion 114b and a recessed portion 114c, which can store predetermined amounts of the liquid, are arranged in series in the flow passage after passing through an end portion 114d of the diluting flow passage 114. The recessed portion 114b functions as a mixing chamber for the blood, the diluent, and the standard hemolytic liquid, wherein the measuring sample, which is allowed to flow thereinto via the diluting flow passage 114, is temporarily stored, and the measuring sample is mixed equivalently or uniformly. The measuring sample is finally prepared in the recessed portion 114b. The corresponding air vent holes 104, 105, which are formed through the cover 100, are arranged on the recessed portion 114b and the recessed portion 114c when the microdevice is formed.

When the measurement is performed by the measuring device, the measuring sample, which is prepared in the recessed portion 114b, is subjected to the counterflow to the diluting flow passage 114 by means of the external force such as the centrifugal force or the like. In accordance with the counterflow, the measuring sample passes through the measuring area MR. Accordingly, the measuring device for measuring the plasma glucose concentration (i.e., the measuring device corresponding to the sensor unit and/or the absorbance meter 85 of the embodiment described above), which is installed for the measuring area MR, can measure the physical property of the measuring sample in order to measure the plasma glucose concentration without being affected by any bubble in the measuring sample. After the measurement, only the diluent is allowed to flow into the diluting flow passage 114. Accordingly, the entire flow passages are washed to perform the preparation of the next measuring sample and the preparation for the measurement.

In this arrangement, when the liquid, which flows through the diluting flow passage 114, arrives at the recessed portion 114b, any bubble may be possibly caught therein because the flow passage is suddenly enlarged, depending on the size and the shape of the recessed portion 114b. In such a situation, the flow control is performed such that the measuring sample, which is prepared in the recessed portion 114b, is once allowed to flow toward the recessed portion 114c, and then the measuring sample, which is contained in the recessed portion 114b, is withdrawn toward the measuring area MR. When the flow of the liquid is controlled as described above, then the bubble, which is caught by the measuring sample in the recessed portion 114b, is excluded or expelled to the recessed portion 114c, and the measuring sample, which does not contain the bubble, is thereafter withdrawn into the measuring area MR. Therefore, it is possible to expect the correct measurement without being affected by the bubble. From this viewpoint, the recessed portion 114c functions as a bubble trap section which traps the bubble contained in the measuring sample.

The measuring apparatuses according to the first embodiment and the first and second modified embodiments described above are provided with the arrangement in which the measuring sample is withdrawn into the measuring area of the supply route 27 (diluting flow passage 114). According to this arrangement, it is possible to solve the problem of the invasion of the bubble into the measuring area as described above, while the following advantages can be obtained.

In the first place, it is possible to carry out the correct baseline measurement for the diluent (liquid for the preparation) in the measurement of the absorbance as explained in the first embodiment and the first and second modified embodiments. That is, in the measuring apparatus as described above, the diluent is supplied to the supply route 27 (diluting flow passage 114) after the completion of the measurement of, for example, the absorbance. Accordingly, the measured measuring sample, which has been withdrawn into (allowed to stay in) the supply route 27 (diluting flow passage 114), can be forcibly allowed to flow toward the downstream side. In other words, the supply route 27 (diluting flow passage 114) can be washed with the diluent. Therefore, when a sufficient amount of the diluent is supplied to the supply route 27 (diluting flow passage 114) after the completion of the measurement, a state is given, in which the interior of the supply route 27 (diluting flow passage 114) is filled with the pure diluent. When the baseline measurement is carried out in this state, it is possible to obtain the correct baseline. However, the baseline measurement is also applicable in relation to the color measurement for a sample based on the transmitted light obtained by transmitting the measuring light through the measuring sample and the concentration measurement for a predetermined component by utilizing the transmitted light as performed in the liquid chromatography.

In the second place, in the first embodiment and the first and second modified embodiments, the supply route 27 (diluting flow passage 114), which is the flow passage for introducing the diluent, also serves as the flow passage for inducing or guiding the measuring sample to the measuring area. Therefore, it is unnecessary to form any inducing flow passage for the measuring sample different from the flow passage for introducing the diluent. This advantage contributes to the miniaturization and the simplification of the measuring apparatus.

In the third place, when any inducing flow passage for the measuring sample, which is different from the flow passage for introducing the diluent, is formed, it is conceived to miniaturize and simplify the measuring apparatus by using the inducing flow passage as the discharging flow passage for discharging the measuring sample as well. In this case, the measuring sample (waste liquid), which is to be discharged, is discharged while passing through the inducing flow passage. Therefore, the interior of the inducing flow passage is in a state of being dirtied by the residue (for example, blood serum). On the contrary, in the case of the arrangement as explained in the first embodiment and the first and second modified embodiments, the measuring sample, which is in the amount required for the measurement, is induced or guided to the flow passage for introducing the diluent (supply route 27, diluting flow passage 114). Therefore, it is possible to reduce the amount of the measuring sample allowed to flow through the flow passage for the measurement, and it is possible to suppress the interior of the flow passage from being dirtied.
[Second Embodiment]
<Other Embodiments>

As described above, the present invention includes, in an embodiment thereof, the computer program for performing the measurement control. Further, a medium, in which the program is recorded on the recording medium readable by the computer, also belongs to the category or concept of the present invention. As for the recording medium in which the program is recorded, the measurement control as described above can be performed by reading and executing the program of the recording medium by the computer.

The recording medium, which is readable by the computer, herein refers to the recording medium in which the information including, for example, the data and the program is stored in accordance with the electrical, magnetic, optical, mechanical, or chemical function, and the information can be read therefrom by the computer. Those included in the recording medium as described above, which are removable from the computer, are exemplified, for example, by the floppy disk (trade name), the magneto-optical disk, CD-ROM, CD-R/W, DVD, Blu-ray Disk, DAT, 8 mm tape, and the memory card. Those provided as the recording medium, which are fixed to the computer, are exemplified, for example, by the hard disk and ROM (Read Only Memory).

What is claimed is:

1. A measuring apparatus for measuring a predetermined physical property of a liquid measuring sample, the measuring apparatus comprising:
   a preparing unit configured to prepare the measuring sample;
   a supply route configured to supply a liquid material to the preparing unit in order to prepare the measuring sample;
   a withdrawing unit configured to withdraw the measuring sample from the preparing unit into the supply route, the measuring sample being prepared by supplying the liquid material to the preparing unit via the supply route; and
   a measuring unit configured to measure the predetermined physical property of the measuring sample withdrawn into the supply route by the withdrawing unit.

2. The measuring apparatus according to claim 1, wherein the measuring unit is configured to measure the predetermined physical property of the measuring sample by means of optical means.

3. The measuring apparatus according to claim 1, wherein the withdrawing unit is configured to withdraw the measuring sample from the preparing unit so that a mixture liquid of the measuring sample and the liquid material contained in the supply route, which is produced when the measuring sample is withdrawn into the supply route, is moved beyond a predetermined measuring area disposed in the supply route in order to perform the measurement by the measuring unit.

4. The measuring apparatus according to claim 1, further comprising:
   a supply route discharge section configured to discharge the measuring sample existing in the supply route to the preparing unit after the predetermined physical property of the measuring sample is measured by the measuring unit; and
   a preparing unit discharge section configured to discharge any liquid contained in the preparing unit to outside of the preparing unit after the discharge performed by the supply route discharge section or in synchronization therewith.

5. The measuring apparatus according to claim 4, wherein the supply route and the preparing unit are communicated with each other via a communication hole which has such a predetermined cross-sectional area that any air contained in the preparing unit does not enter the supply route when the discharge by the supply route discharge section is completed, the liquid contained in the preparing unit is discharged by the preparing unit discharge section, and a liquid level in the preparing unit is lower than a position of communication between the supply route and the preparing unit.

6. The measuring apparatus according to claim 1, wherein the measuring sample is prepared by mixing, in the preparing unit, blood, a hemolytic agent which hemolyzes the blood, and a diluent which is supplied as the liquid material via the supply route to the preparing unit and which dilutes the blood.

7. The measuring apparatus according to claim 6, wherein the measuring unit is configured to measure a hemoglobin concentration in the measuring sample withdrawn into the supply route by the withdrawing unit, as the predetermined physical property by means of optical means.

8. The measuring apparatus according to claim 7, further comprising:
   a sample glucose concentration measuring unit configured to measure a glucose concentration of the measuring sample; and
   a plasma glucose concentration calculating unit configured to calculate a plasma glucose concentration of the blood on the basis of the glucose concentration measured by the sample glucose concentration measuring unit and the hemoglobin concentration measured by the measuring unit.

9. The measuring apparatus according to claim 8, wherein the sample glucose concentration measuring unit is configured to measure the glucose concentration of the measuring sample contained in the preparing unit in a state of being exposed to the measuring sample in the preparing unit.

10. The measuring apparatus according to claim 8, wherein the sample glucose concentration measuring unit is configured to measure the glucose concentration of the measuring sample in the supply route in a state of being exposed to the measuring sample withdrawn into the supply route by the withdrawing unit.

11. The measuring apparatus according to claim 10, wherein the sample glucose concentration measuring unit is installed in the supply route between the measuring unit and the preparing unit.

12. A measuring method for measuring a predetermined physical property of a liquid measuring sample by a measuring device having a preparing unit, a supply route, a withdrawal unit and a measuring unit, the measuring method comprising:
   supplying a liquid material to the preparing unit using the supply route;
   using the withdrawing unit and withdrawing the measuring sample from the preparing unit into the supply route, the measuring sample being prepared by supplying the liquid material to the preparing unit via the supply route; and
   using the measuring unit and measuring the predetermined physical property of the measuring sample withdrawn into the supply route.

13. The measuring method according to claim 12, wherein the predetermined physical property of the measuring sample is measured by optical means in the measuring.

14. The measuring method according to claim 12, further comprising:
discharging the measuring sample existing in the supply route to the preparing unit after measuring the predetermined physical property of the measuring sample in the measuring; and
discharging any liquid contained in the preparing unit to outside of the preparing unit after the discharge performed in the supply route discharging or in synchronization therewith.

15. A non-transitory computer readable medium storing a measuring program for measuring a predetermined physical property of a liquid measuring sample prepared in a preparing unit by supplying a liquid material to the preparing unit via a supply route by means of a computer, the measuring program allowing the computer to execute:
withdrawing the measuring sample from the preparing unit into the supply route, the measuring sample being prepared by supplying the liquid material to the preparing unit via the supply route; and
measuring the predetermined physical property of the measuring sample withdrawn into the supply route in the withdrawing.

16. The non-transitory computer readable medium storing the measuring program according to claim 15, wherein the predetermined physical property of the measuring sample is measured by optical means in the measuring.

17. The non-transitory computer readable medium storing the measuring program according to claim 15, wherein the measuring program allows the computer to further execute:
discharging the measuring sample existing in the supply route to the preparing unit after measuring the predetermined physical property of the measuring sample in the measuring; and
discharging any liquid contained in the preparing unit to outside of the preparing unit in synchronization with the discharge of the measuring sample from the supply route.

18. A measuring system for measuring a predetermined physical property of a liquid measuring sample, the measuring system comprising:
a preparing device which prepares the measuring sample;
a supply route which supplies a liquid material to the preparing device in order to prepare the measuring sample;
a withdrawing device which withdraws the measuring sample from the preparing device into the supply route, the measuring sample being prepared by supplying the liquid material to the preparing device via the supply route; and
a measuring device which measures the predetermined physical property of the measuring sample withdrawn into the supply route by the withdrawing device.

19. The measuring system according to claim 18, wherein the measuring device measures the predetermined physical property of the measuring sample by means of optical means.

20. The measuring system according to claim 19, wherein the withdrawing device withdraws the measuring sample from the preparing device so that a mixture liquid of the measuring sample and the liquid material contained in the supply route, which is produced when the measuring sample is withdrawn into the supply route, is moved beyond a predetermined measuring area disposed in the supply route in order to perform the measurement by the measuring device.

21. The measuring system according to claim 1, wherein the supply route includes a measurement area for the measuring unit, and
the measurement area is filled with at least one of the measuring sample, the liquid material, and a mixture liquid of the measuring sample and the liquid material during the supplying of the liquid material to the preparing unit, the withdrawing of the measuring sample into the supply route, and the measurement by the measuring unit.

* * * * *